(12) United States Patent
Shurney

(10) Patent No.: US 9,205,038 B2
(45) Date of Patent: Dec. 8, 2015

(54) BRIGHTENER-CONTAINING HAIR RELAXER

(71) Applicant: Glenn Shurney, Chicago, IL (US)

(72) Inventor: Glenn Shurney, Chicago, IL (US)

( * ) Notice: Subject to any disclaimer, the term of this patent is extended or adjusted under 35 U.S.C. 154(b) by 256 days.

(21) Appl. No.: 13/724,534

(22) Filed: Dec. 21, 2012

(65) Prior Publication Data

US 2014/0178322 A1    Jun. 26, 2014

(51) Int. Cl.
*A61Q 5/04*    (2006.01)
*A61K 8/46*    (2006.01)

(52) U.S. Cl.
CPC .... *A61K 8/46* (2013.01); *A61Q 5/04* (2013.01)

(58) Field of Classification Search
CPC .................................. A61K 8/46; A61Q 5/04
See application file for complete search history.

(56) References Cited

U.S. PATENT DOCUMENTS

| | | | | |
|---|---|---|---|---|
| 3,892,845 | A * | 7/1975 | Cunningham | A61K 8/23 132/208 |
| 5,293,885 | A * | 3/1994 | Darkwa | A61K 8/447 132/203 |
| 5,565,216 | A | 10/1996 | Cowsar et al. | |
| 7,754,194 | B2 | 7/2010 | Cannell et al. | |
| 2002/0159962 | A1 | 10/2002 | Cannell et al. | |
| 2004/0253283 | A1 | 12/2004 | Muller et al. | |
| 2010/0300471 | A1 | 12/2010 | Malle et al. | |

OTHER PUBLICATIONS

PCT/US2013/076637 International Search Report, and Written Opiunion.
Corbett and Gamson, *J. Chem. Soc. Perkin II*, 1531-1537 (1972).
Cannell, *Clin Dermatol*, 6(3):71-82 (1988).
DE *Natural*, Design Essentials, McBride Research Laboratories, Inc, Decatur, GA, USA 2013.

* cited by examiner

*Primary Examiner* — Sean Basquill
*Assistant Examiner* — Andrew S. Rosenthal
(74) *Attorney, Agent, or Firm* — Husch Blackwell LLP

(57) ABSTRACT

An improved aqueous human hair relaxer composition is disclosed that contains effective amounts of active human hair straightening ingredients and excipients, and having a pH value of about 12 to about 14, whose improvement comprises the incorporation of a dissolved or dispersed discoloration-inhibiting effective amount of alpha-hydroxy-$C_1$-$C_6$ sulfinate of Formula I, below, where

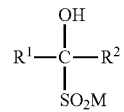

I $R^1$, $R^2$ and M substituents are defined within. A method of using such a composition to straighten human hair without the discoloration to grey or white hair that normally accompanies relaxation is also disclosed.

19 Claims, No Drawings

BRIGHTENER-CONTAINING HAIR RELAXER

TECHNICAL FIELD

This invention relates to the straightening or relaxing of human hair, and particularly to the relaxation of grey or white hair without the discoloration or yellowing of the hair that often occurs with such processes.

BACKGROUND ART

A hair fiber, a keratinous material, contains proteins or polypeptides that are bonded together (cross-linked) by disulfide bonds (—S—S—). A disulfide bond that is formed from the sulfhydryl groups (—SH) of two cysteine residues results in a disulfide-containing cystine amino acid residue. The hair straightening or relaxing process is a chemical process that principally acts by altering cystine disulfide chemical bonds in the hair to form lanthionine, a monosulfide analog of cystine, that can be viewed as being composed of two alanine residues that are cross-linked on their β-carbon atoms by a thioether linkage.

Aqueous alkali containing hair relaxing or straightening compositions are known in the art. Such compositions usually have a pH value of about 12 to 14 due to the presence of one or more of a water-soluble alkali metal or alkaline earth material such as lithium hydroxide, sodium hydroxide, potassium hydroxide, calcium hydroxide, barium hydroxide, or a nitrogen base such as guanidinium hydroxide, and are most frequently formulated as emulsified or creamy, viscous preparations so that once applied to the user's (subject's) hair, they will not drip onto the skin or into the eyes.

Hair relaxers are usually supplied as "with base" or "no-base" formulations. A "with base" formulation is generally supplied in two packages; one containing the oleaginous base and one containing a thickened aqueous composition of alkaline materials. For those products with a base, the oleaginous base such as one or more of petrolatum, mineral oil and lanolin is first applied to the user's scalp as a protective layer and hair followed by application of the thickened aqueous alkaline material that then relaxes the hair.

No-base formulations are one package systems in which the aqueous and oleaginous materials are co-emulsified. The no-base formulations are applied directly to the user's hair without a prior pretreatment of the scalp.

One type of no-base hair relaxer formulation contains as the active hair straightening agent an alkali metal hydroxide, typically a caustic base, such as sodium hydroxide or potassium hydroxide. When a relatively low active level of about 1.5 to about 2.5 weight percent of caustic base is used, a protective base is applied only to the hairline to protect the skin around the forehead, ears and neckline, with the remainder of the scalp being directly treated with the relaxer. Such no-base formulations preferably have some of the protective oleaginous material emulsified in an aqueous composition, and are supplied in a "single product" kit.

Most no-base cream products are aqueous emulsions in which water is the continuous phase, i.e., oil-in-water emulsions, because they are easier to rinse from the hair. Instability or de-emulsification can result because of the relatively high concentration of oleaginous material present dispersed in the water phase, which provides a destabilized cream product having two distinctly visible phases. Although such destabilized products can be used, they must be remixed before using in an attempt to assure the user that the active ingredients are at the proper levels in the portion being used. However, such mixing, even though done thoroughly by hand, often does not provide the user with consistent relaxation results, can cause skin irritation or result in increased hair breakage. Product destabilization and resulting consumer dissatisfaction are among the chief complaints in the industry.

A more recently developed type of no-base hair relaxer formulation is commonly called a "no-lye" hair relaxer. With a no-base, no-lye relaxer, a protective base need not be applied to the scalp and can does need to be applied to the hairline. The term "no-lye" means that the active hair straightening agent is an organic chemical base instead of caustic base, although some amount of caustic base can be present.

In commercial practice, the relatively strong organic chemical base, guanidine is usually present in the form of guanidine hydroxide. However, guanidine hydroxide is not generally stable for long periods in aqueous solutions. Consequently, it must be prepared fresh just before using.

Guanidine hydroxide is generally prepared by reacting an inorganic chemical base such as an alkaline earth hydroxide with an aqueous solution of a salt of guanidine, where the anion of this guanidine salt forms a precipitate with the cation of the alkaline earth hydroxide. In commercially available products of this type, the guanidine hydroxide is generally prepared using guanidine carbonate and calcium hydroxide.

When such a no-lye hair relaxer is commercially used, the product is supplied as a two-part kit. One part contains the guanidine carbonate in substantially liquid form and is commonly called the "activator." The other part contains relatively high amounts of about 4 to about 7 percent calcium hydroxide emulsified in a cosmetic cream base. Prior to using, the consumer or beautician mixes the cream and activator portions of the kit together. The resulting no-lye hair relaxer is then relatively promptly (preferably within 24 hours) applied to the hair. Many of the foregoing emulsion stability problems were overcome in U.S. Pat. No. 4,390,033 and No. 4,237,910 both to our assignee, by the use of certain lipophilic organically-modified hectorite clay gellants. A relatively high amount (about 8 to about 12 weight percent) of the hectorite clay gellant is generally required to achieve a relatively stiff viscous cream.

As noted above, no-base hair relaxers are desirably formulated as emulsified viscous creams so that once applied to the user's hair, they will not drip onto the skin or into the eyes of the person receiving a hair straightening procedure. The cosmetic cream base portion of a no-lye hair relaxer must also mix easily with the activator solution without thinning to a soft runny cream. Additionally, an ideal no-base hair relaxer cream must be easy to remove from the hair at the end of the straightening or relaxer procedure.

A result of a hair no-lye straightening treatment can be that residue of the alkaline composition remains in the hair causing the hair to be dull, stiff, crusty or gritty. For example, when a calcium hydroxide-based product is used in a hair straightening treatment, calcium deposits are left on the hair which leaves a white residue or unattractive "whitening" or "ashing" that remains in the hair because divalent metals like calcium have a relatively good affinity to keratin. A decalcifying shampoo is subsequently needed to remove the ashing. The presence of the calcium deposits also causes the hair have a dry and gritty feeling and a dull appearance. These problems have been at least partially dealt with by use of acidic treatment of the hair as disclosed in U.S. Pat. No. 7,226,585 and No. 7,754,194.

One problem with which the art has not dealt is the discoloration of naturally grey or white hair that is treated with a relaxer composition. That discoloration changes the grey or white hair to colors ranging from yellow, to brown and green tints. The chemical basis for these discolorations is not presently known. The invention disclosed below provides one solution to this problem of discoloration.

BRIEF SUMMARY OF THE INVENTION

The present invention contemplates a composition and a method for relaxing human hair, and particularly naturally grey or white hair, that maintains the hair's original color and does not cause the discoloration caused by other relaxers. The present invention can also be used on naturally dark colored hair, but the benefits of inhibition of discoloration will largely be invisible due to the natural coloration of the hair masking discoloration that might occur in the absence of use of a relaxer of the invention. Thus, a composition and method are particularly useful for relaxing human hair that is naturally grey or white.

One embodiment of the invention contemplates an improved hair relaxer comprise an aqueous composition that contains a human hair straightening effective amount of active human hair straightening ingredients and excipients having a pH value of about 12 to about 14. The contemplated improvement comprises the inclusion of a naturally grey or white human hair discoloration-inhibiting amount of an alpha-hydroxy-$C_1$-$C_6$-sulfinate of Formula I, below, dissolved or dispersed in the relaxer in

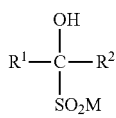

I addition to the water, active straightening ingredients and a cosmetically useful amount of one or more excipients. An alpha-hydroxy-$C_1$-$C_6$-sulfinate also referred to as a brightener is present in an amount that provides an equivalent of about 4 to about 6 weight percent of sodium sulfinomethanolate based upon the total weight of relaxer composition applied to the hair.

In a compound of Formula I, $R^1$ and $R^2$ are the same or different and are hydrogen (hydrido) or hydrocarbyl, or one of $R^1$ and $R^2$ is carboxy or carboxy-substituted hydrocarbyl and the other of $R^1$ and $R^2$ is hydrido or hydrocarbyl that together ($R^1+R^2$) contain a total of five carbon atoms, or $R^1$ and $R^2$ together with the depicted carbon atom form a ring structure that can contain up to six carbon atoms, and M is a proton or a cosmetically acceptable cation such as an ammonium ion, a monovalent metal ion or an equivalent of a divalent metal ion of the Groups Ia, IIa, IIb, IVa or VIIIb of the Periodic Table of the Elements.

A particularly preferred compound of Formula I is the $C_1$ alpha-hydroxy-$C_1$-$C_6$ sulfinate, sulfinomethanolate, whose chemical formula is shown in Formula III where M is as discussed above, or a cosmetically acceptable salt, e.g., sodium or potassium salt.

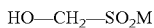

III

One preferred group of compounds of Formula I are the compounds of Formula II, below, that are

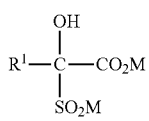

II alpha-hydroxy-$C_1$-$C_6$-carboxy sulfinate compounds. $R^1$ of Formula II can be hydrido or can contain up to four carbon atoms, and M is a proton or a cosmetically acceptable cation as previously discussed. One particularly preferred compound of Formula II is the $C_2$ alpha-hydroxy-$C_1$-$C_6$-carboxy sulfinate in which $R^1$ is hydrido so that the compound is 2-hydroxy-2-sulfinatoacetic acid where M is a proton, whose structure is shown in Formula IV or a

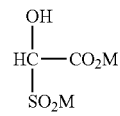

IV cosmetically acceptable salt of that acid such as the disodium or dipotassium salt.

A relaxer composition can be provided in many different formats, and this invention is applicable to all of them. Thus, one aspect of the invention contemplates an aqueous no-lye relaxer that can comprise i) a cosmetically useful amount of one or more excipients, ii) calcium hydroxide in a concentration of about 1.5 to about 5 percent by weight relative to the total weight of the composition and guanidine hydroxide in concentration of about 3 to about 8 percent by weight as active human hair straightening ingredients that are mixed with iii) an alpha-hydroxy-$C_1$-$C_6$-hydrocarbyl sulfinate present in an amount that provides an equivalent of about 4 to about 6 weight percent of sodium sulfinomethanolate based upon the total weight of relaxer composition applied to the hair. Use of such a composition to relax hair produces the desired effect of keeping the black, brown or red hair its original color, while maintaining white or grey hair to white or grey, respectively.

Another aspect of the invention contemplates an aqueous lye relaxer comprising i) a cosmetically useful amount of one or more excipients, ii) sodium hydroxide in a concentration of about 0.5 to about 3 percent by weight relative to the total weight of the composition, guanidine hydroxide in concentration of about 0.05 to about 3 percent by weight as active human hair straightening ingredients that are mixed with iii) an alpha-hydroxy-$C_1$-$C_6$-hydrocarbyl sulfinate present in an amount that provides an equivalent of about 4 to about 5 weight percent of sodium sulfinomethanolate based upon the total weight of relaxer composition applied to the hair. Again, use of such a composition to relax hair produces the desired effect of keeping the black, brown or red hair its original color, while maintaining white or grey hair to white or grey, respectively.

Still another aspect of the invention contemplates an aqueous no-lye relaxer comprising i) a cosmetically useful amount of one or more excipients, ii) potassium hydroxide in a concentration ranging about 1 to about 1.55 by weight relative to the total weight of the composition, and guanidine hydroxide in concentration of about 0.1 to about 5 percent by weight as active human hair straightening ingredients that are mixed with iii) an alpha-hydroxy-$C_1$-$C_6$-hydrocarbyl sulfinate present in an amount that provides an equivalent of about 4 to about 5 weight percent of sodium sulfinomethanolate based upon the total weight of relaxer composition applied to the hair. Yet again, use of such a composition to relax hair produces the desired effect of keeping the black, brown or red hair its original color, while maintaining white or grey hair to white or grey, respectively.

An above contemplated relaxer composition also contains one or more excipients, particularly when applied to a subject's hair. Illustrative excipients include one or more thickening agents, oleaginous materials, gellants, emulsifiers, colorants and odorants. Illustrative excipients are discussed hereinafter.

Also contemplated is an improved method of straightening human hair, and particularly white or grey human hair. In that improved method, an aqueous hair relaxer composition containing active straightening ingredients and excipients as discussed above is applied to the hair, the hair is physically smoothed and maintained smoothed for a time period sufficient for hair straightening to occur, typically about 5 to about 30 minutes, rinsed, shampooed, set and dried. The contemplated improvement comprises using a relaxer composition that contains an alpha-hydroxy-$C_1$-$C_6$-hydrocarbyl sulfinate present in an amount that provides an equivalent of about 4 to about 6 weight percent of sodium sulfinomethanolate of the total relaxer composition applied to the hair in addition to the active straightening ingredients and excipients. Any of the before-described relaxer compositions that contain an alpha-hydroxy-$C_1$-$C_6$-hydrocarbyl sulfinate as discussed can be used in a contemplated method.

As used herein, the phrase "active human hair straightening ingredients" is meant to include the basic (alkaline) ingredients such as sodium hydroxide, calcium hydroxide and guanidinium hydroxide that carry out the chemistry of the hair straightening process. The word "excipient" is used to encompass the other, non-active ingredients, other than water and the alpha-hydroxy-$C_1$-$C_6$-hydrocarbyl sulfinate that provide an auxiliary function for the active ingredients such suspending, thickening, dispersing, stabilizing, emollient character, scalp protection for the user and the like. One or more excipients are present in a "cosmetically useful amount", that is, an amount that is useful to provide a product with an appropriate viscosity, stability, emollient, scalp protection and the like as are well known in the hair relaxing industry.

For convenience, the term "no-lye cream base" as used herein means the cosmetic cream base portion of the foregoing kit containing alkaline earth hydroxide. The term "activator" means the substantially liquid portion of a kit containing the organic chemical base, and the "no-lye hair relaxer" means the resulting admixture of the foregoing no-lye cream base and activator. The term "no-base hair relaxer cream," refers generally to a highly alkaline (pH about 12 to about 14) hair straightening product whether supplied as a single product or as a two-product kit.

The term "phase-stable" cream refers to an emulsion composition that shows substantially no visible separation into distinct phases on aging. Thus, phase stability refers to physical stability and is not intended to refer to the chemical stability of the non-alkaline individual ingredients against decomposition by or interaction with the alkaline material under highly alkaline conditions over a relatively long lifetime.

The present invention has several benefits and advantages.

One salient benefit is that use of the invention in hair straightening of white or grey hair inhibits the discoloration that otherwise usually accompanies a relaxer straightening treatment.

An advantage of the invention is that a required amount of alpha-hydroxy-$C_1$-$C_6$-hydrocarbyl sulfinate that provides an equivalent of about 4 to about 6 weight percent of sodium sulfinomethanolate based upon the total weight of relaxer composition applied to the hair can be provided independently of a manufactured hair relaxer to be admixed with the commercial product prior to use.

A benefit related to that immediately above is that a contemplated alpha-hydroxy-$C_1$-$C_6$-hydrocarbyl sulfinate is typically a solid that is highly water-soluble and be admixed with a commercial product prior to use.

Still further benefits and advantages will become apparent to those skilled in the art from the disclosures that follow.

DETAILED DESCRIPTION OF THE INVENTION

The present invention contemplates a composition and a method for relaxing human hair, particularly naturally grey or white hair, that maintains the hair's original color and does not cause the discoloration of naturally grey or white hair caused by other relaxers. The present invention can also be used on naturally dark colored hair, but the benefits of inhibition of discoloration will largely be invisible due to the natural coloration of the hair masking discoloration that might occur in the absence of use of a relaxer of the invention. Thus, a composition and method are particularly useful for relaxing human hair that is naturally grey or white.

A contemplated composition is an improved human hair relaxer composition that further contains dissolved or dispersed therein a discoloration-inhibiting effective amount of alpha-hydroxy-$C_1$-$C_6$ sulfinate of Formula I (a brightener), below, or a

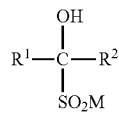

I cosmetically acceptable salt thereof in which $R^1$ and $R^2$ are the same or different and are hydrogen (hydrido) or hydrocarbyl, or one of $R^1$ and $R^2$ is carboxy or carboxy-substituted hydrocarbyl and the other is hydrido or hydrocarbyl that together ($R^1$+$R^2$) contain a total of five carbon atoms, or $R^1$ and $R^2$ together with the depicted carbon atom form a ring structure that can contain up to six carbon atoms, and M is a proton or a cosmetically acceptable cation such as an ammonium ion, a monovalent metal ion or an equivalent of a divalent metal ion of the Groups Ia, IIa, IIb, IVa or VIIIb of the Periodic Table of the Elements.

In addition to the naturally grey or white human hair discoloration-inhibiting amount of an alpha-hydroxy-$C_1$-$C_6$ sulfinate of Formula I, a contemplated improved relaxer contains water, active straightening ingredients and a cosmetically useful amount of one or more excipients. A naturally grey or white human hair discoloration-inhibiting amount of an alpha-hydroxy-$C_1$-$C_6$-sulfinate is typically present in an amount that provides an equivalent of about 4 to about 6 weight percent of sodium sulfinomethanolate based upon the total weight of relaxer composition applied to the hair.

It is contemplated that the discoloration-inhibiting effective amount of alpha-hydroxy-$C_1$-$C_6$ sulfinate that is present in a contemplated improved relaxer composition can be added to any hair relaxer composition that is otherwise ready for on-head use. Thus, the relaxer can be a base or no-base composition, a lye or no-lye composition.

Alpha-Hydroxy-$C_1$-$C_6$ Sulfinate

An alpha-hydroxy-$C_1$-$C_6$ sulfinate brightener compound useful in the present invention corresponds in structure to Formula I, below, where $R^1$ and $R^2$ are the same or

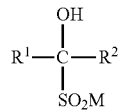

I different and are hydrogen (hydrido) or hydrocarbyl, or one of $R^1$ and $R^2$ is carboxy or carboxy-substituted hydrocarbyl and the other of $R^1$ and $R^2$ is hydrido or hydrocarbyl that together ($R^1$+$R^2$) contain a total of five carbon atoms, or $R^1$ and $R^2$ together with the depicted carbon atom form a ring structure that can contain up to six carbon atoms. A contemplated hydrocarbyl group can be straight or branched chain or cyclic.

M is a proton or a cosmetically acceptable cation such as an ammonium ion, a monovalent metal ion or an equivalent of a divalent metal ion of the Groups Ia, IIa, IIb, IVa or VIIIb of the Periodic Table of the Elements. The reader is directed to Berge, 1977 J. Pharm. Sci. 68(1):1-19 for lists of commonly used pharmaceutically acceptable acids and bases that also form cosmetically acceptable salts with a contemplated alpha-hydroxy-$C_1$-$C_6$-sulfinate compound.

As used herein, the term "hydrocarbyl" is a short hand term for a non-aromatic group that includes straight and branched chain aliphatic as well as alicyclic groups or radicals that contain only carbon and hydrogen. Inasmuch as alicyclic groups are cyclic aliphatic groups, such substituents are deemed hereinafter to be subsumed within the aliphatic groups. Thus, alkyl, alkenyl and alkynyl groups are contemplated, whereas aromatic hydrocarbons such as phenyl and naphthyl groups, which strictly speaking are also hydrocarbyl groups, are referred to herein as aryl groups, substituents, moieties or radicals, as discussed hereinafter. Where a specific aliphatic hydrocarbyl substituent group is intended, that group is recited; i.e., $C_1$-$C_4$ alkyl, methyl or pentenyl. Exemplary hydrocarbyl groups contain a chain of 1 to about 5 carbon atoms, and preferably 1 to about 4 carbon atoms.

A particularly preferred hydrocarbyl group is an alkyl group. As a consequence, a generalized, but more preferred substituent can be recited by replacing the descriptor "hydrocarbyl" with "alkyl" in any of the substituent groups enumerated herein.

Examples of straight and branched chain alkyl groups include methyl, ethyl, n-propyl, isopropyl, n-butyl, isobutyl, sec-butyl, tert-butyl, pentyl, iso-amyl, and hexyl. Examples of suitable straight and branched chain alkenyl radicals include ethenyl (vinyl), 2-propenyl, 3-propenyl, 1,4-pentadienyl, 1,4-butadienyl, 1-butenyl, but-2-enyl, 3-methyl-2-butenyl, and the like. Examples of straight and branched chain alkynyl groups include ethynyl, 2-propynyl, prop-2-ynyl, 1-butynyl, 2-methylbut-3-ynyl, 3-butynyl. Illustrative cyclic groups formed when $R^1$ and $R^2$ together with the depicted carbon atom of Formula I form a ring structure include cyclohexyl, cyclopentyl, 3-methylcyclopentenyl, and cyclohexenyl.

Thus, where both of $R^1$ and $R^2$ are hydrido, a useful alpha-hydroxy-$C_1$-$C_6$-sulfinate of Formula I is the $C_1$ alpha-hydroxy-$C_1$-$C_6$ sulfinate, sulfinomethanolate, whose chemical formula is shown in Formula III, below, where M is as discussed above

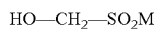     III or a cosmetically acceptable salt thereof such as the sodium or potassium salt. Sodium sulfinomethanolate is a particularly preferred alpha-hydroxy-$C_1$-$C_6$-sulfinate salt and is commercially available as the dihydrate in the form of a white solid powder from EMD Chemicals Inc., of Gibbstown, N.J., and also from Bruggemann Chemical US, Inc. of Philadelphia, Pa.

Another preferred group of compounds of Formula I are the compounds of Formula II, below,

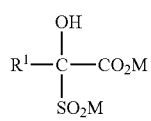     II that are alpha-hydroxy-$C_1$-$C_6$-carboxy sulfinate compounds. $R^1$ of Formula II can be hydrido or can contain up to four carbon atoms, and M is a proton or a cosmetically acceptable cation as previously discussed. One particularly preferred compound of Formula II is the $C_2$ alpha-hydroxy-$C_1$-$C_6$-carboxy sulfinate in which $R^1$ is hydrido so that the compound is 2-hydroxy-2-sulfinatoacetate, whose structure is shown in Formula IV, below, where M is a proton or a

     IV cosmetically acceptable salt of that acid such as the disodium or dipotassium salt, as was discussed above. Disodium 2-hydroxy-2-sulfinatoacetate mixed with 2-hydroxy-2-sulfoacetate and sodium sulfite is commercially available under the designation Bruggerlite® FF6M from Bruggemann Chemicals US, Inc. of Philadelphia, Pa.

That mixture of compounds and their syntheses are discussed in U.S. Pat. No. 6,211,400 and its divisional U.S. Pat. No. 6,586,622, and claimed in claim 9 of U.S. Pat. No. 6,211,400. That claimed composition contained 2-hydroxy-2-sulfinatoacetic acid, 40-73% by weight disodium salt, 2-hydroxy-2-sulfonatoacetic acid, 2-7% by weight disodium salt, sodium sulfite 0-33% by weight, and water 5-30% by weight.

Following the procedures set out in U.S. Pat. No. 6,211,400, a contemplated alpha-hydroxy-$C_1$-$C_6$-sulfinate of Formulas I-IV can be prepared by the reaction of a dithionite ($S_2O_4^{-2}$) ion-providing reagent such as sodium dithionite with a $C_1$-$C_6$-aldehyde or ketone, or a $C_1$-$C_6$-carbonyl group-containing carboxylate in a basic aqueous medium.

The alpha-hydroxy-$C_1$-$C_6$-sulfinate compounds disclosed in the above patents are said to be useful as reducing agents, particularly in conjunction with a peroxide as an aqueous emulsion polymerization that does not provide yellowing discoloration of the polymer.

Compositions

One embodiment of the invention contemplates an improved aqueous hair relaxer having a pH value of about 12 to about 14 comprising i) an aqueous composition of active human hair straightening ingredient, ii) a cosmetically useful amount of excipient, and iii) an improvement-providing naturally grey or white human hair discoloration-inhibiting amount of an alpha-hydroxy-$C_1$-$C_6$ sulfinate compound of previously described Formula I dissolved or dispersed therein. Thus, a contemplated improved aqueous relaxer composition contains usual relaxer components in their usual amounts and additionally contains the alpha-hydroxy-$C_1$-$C_6$ sulfinate.

In a preferred embodiment, the alpha-hydroxy-$C_1$-$C_6$ sulfinate is present in an amount that provides an equivalent of about 4 to about 6 weight percent of sodium sulfinomethanolate based upon the total weight of relaxer composition applied to the hair. The $C_1$ alpha-hydroxy-$C_1$-$C_6$ sulfinate, sodium sulfinomethanolate, is most preferred.

The phrase "provides an equivalent of about 4 to about 6 weight percent of sodium sulfinomethanolate" is utilized to account for the differing molecular weights of ingredients having different chain lengths among the $C_1$-$C_6$ groups and the possible inclusion of a carboxyl group, as well for different crystal forms that can contain one or more molecules of water per molecule of alpha-hydroxy-$C_1$-$C_6$ sulfinate. Thus, knowing the molecular weight of a given alpha-hydroxy-$C_1$-$C_6$ sulfinate or crystal form that is to be used, and comparing that weight to the molecular weight of sodium sulfinomethanolate, the skilled worker can readily formulate a useful composition.

Active Human Hair Straightening Ingredient

A contemplated relaxer contains an "active human hair straightening ingredient". That ingredient is one or more highly alkaline (basic) components such as a water-soluble alkali metal hydroxide such as lithium hydroxide, sodium hydroxide, and potassium hydroxide, or an alkaline earth hydroxide such as calcium hydroxide, barium hydroxide, or an amidino group-containing [—C(=NH)—NH$_2$] nitrogen base such as guanidinium hydroxide. A precursor to an alkali metal hydroxide or alkaline earth hydroxide such as a corresponding metal oxide can also be used.

One preferred aspect of the invention contemplates an aqueous no-lye relaxer that can comprise a hair straightening amount of one or more excipients, in which calcium hydroxide is an active human hair straightening ingredient that is present at a concentration of about 1.5 to about 5 percent by weight relative to the total weight of the composition mixed with guanidine hydroxide at a concentration of about 3 to about 8 percent by weight as active human hair straightening ingredients that are mixed with an alpha-hydroxy-$C_1$-$C_6$ sulfinate present in an amount that provides an equivalent of about 4 to about 6 weight percent of sodium sulfinomethanolate based upon the total weight of relaxer composition applied to the hair. Use of such a composition to relax hair produces the desired effect of keeping the black, brown or red hair in its original color, while maintaining white or grey hair to white or grey, respectively, as compared to the latter hair turning yellow to greenish brown.

Another aspect of the invention contemplates a lye relaxers comprising sodium hydroxide in a concentration of about 0.5 to about 3 percent by weight relative to the total weight of the composition, guanidine hydroxide in concentration of about 0.05 to about 3 percent by weight active human hair straightening ingredients that are mixed with an alpha-hydroxy-$C_1$-$C_6$ sulfinate present in an amount that provides an equivalent of about 4 to about 5 weight percent of sodium sulfinomethanolate based upon the total weight of relaxer composition applied to the hair. Again, use of such a composition to relax hair produces the desired effect of keeping the black, brown or red hair its original color, while maintaining white or grey hair to white or grey, respectively.

Still another aspect of the invention contemplates a no-lye relaxer comprising potassium hydroxide in a concentration ranging about 1 to about 1.55 by weight relative to the total weight of the composition, and guanidine hydroxide in concentration of about 0.1 to about 5 percent by weight as active human hair straightening ingredients that are mixed with an alpha-hydroxy-$C_1$-$C_6$ sulfinate present in an amount that provides an equivalent of about 4 to about 5 weight percent of sodium sulfinomethanolate based upon the total weight of relaxer composition applied to the hair. Yet again, use of such a composition to relax hair produces the desired effect of keeping the black, brown or red hair its original color, while maintaining white or grey hair to white or grey, respectively.

A contemplated hair relaxing composition contains a human hair straightening effective amount of a water-soluble active human hair straightening ingredient that is an alkaline material capable of both bringing the pH of the composition to a value of about 12 to about 14, and acting as the sole hair relaxing agent. Typically, one or more such agents are used. The amount of any particular active human hair straightening ingredient used in a relaxer composition depends upon an number of factors such as the specific agent used, e.g., sodium hydroxide, calcium hydroxide guanidinium hydroxide, and whether one or more agents are utilized in a particular composition.

Alkali metal hydroxides, including sodium hydroxide, potassium hydroxide and lithium hydroxide can be used as the water-soluble alkaline caustic material. Sodium hydroxide (lye) is preferred in many products and can be present in amounts from about 0.5 to about 3 weight percent of the total composition, preferably from about 1.5 to about 2.5 weight percent.

A no-base, no-lye hair relaxer is typically an aqueous emulsion that preferably contains as the active human hair straightening ingredient (hair-relaxing agent), a water-soluble alkaline material that is preferably a strong organic base, such as an amidino group-containing base like guanidinium hydroxide also referred to in the art as guanidine hydroxide.

Guanidinium hydroxide is typically made just before application of the composition to the hair by the reaction of a guanidine salt such as guanidinium carbonate with calcium hydroxide. In this embodiment, calcium hydroxide is present in the emulsified no-lye cream base, and guanidinium carbonate, in a separate aqueous activator solution, is combined with the emulsion just before use. Alternatively, the guanidinium carbonate can be included in the emulsion and calcium hydroxide is added just before use in an aqueous suspension. Other alkaline earth hydroxides, such as barium or strontium hydroxide can be used in place of calcium hydroxide to release free guanidine from guanidine carbonate. Alkaline earth oxides can also be used, producing hydroxides when added to water.

The amount of guanidine in the final composition is about 3 to about 8 percent by weight of the total weight of the composition. Guanidine concentrations within this range are obtained from a corresponding guanidinium carbonate concentration along with a calcium hydroxide concentration in the final mixture of about 1.5 to about 5 percent by weight.

Other amidino group-containing organic bases that can be used in place of guanidine, include N-methyl guanidine, dimethylaminoguanidine (sym. and asym.), acetamidine, dimethylaminoamidine, and aminoamidine. The organic base can be liberated from salts other than the carbonate salt, such as from a sulfate or sulfite salt. In general, the emulsified composition can contain a water-soluble salt of a strong organic base with an anion capable of being precipitated by an alkaline earth metal ion under alkaline conditions.

Excipients

Illustrative excipients include one or more thickening agents, oleaginous materials, gellants, emulsifiers, colorants and odorants. These components are present in a cosmetically useful amount. Such an amount is that which accomplishes the desired cosmetic result such as emulsifying the scalp-protecting oleaginous material, and/or thickening the composition to minimize dripping of the composition, or to provide an attractive odor or the like. The excipients typically constitute about 20 to about 50 percent by weight of the total relaxer composition, with water constituting about 40 to about 70 weight percent of the composition, and the active human hair straightening ingredient and alpha-hydroxy-$C_1$-$C_6$ sulfinate constituting most of the remainder of the composition as noted before.

One particularly useful group of excipients are organically-modified hectorite clay gellants, such as those available from Rheox Inc., Highstown, N.J., that are available in preparations designed both for use in aqueous systems (hydrophilic) and in oil dispersions (lipophilic). These materials and their use in hair relaxer compositions at concentrations of about 2 to about 30 weight percent, and preferably at about 8 to about 20 weight percent, are disclosed in one or more of U.S. Pat. No. 5,068,101, No. 4,390,033 and No. 4,237,910.

Those gellants designed for use in gelling aqueous systems include highly purified montmorillonite clays as well as hectorite clays modified with hydroxyethyl cellulose and other optional agents. Illustrative of these hydrophilic gellants are a hydroxyethyl cellulose-modified hectorite clay gellant trademark named Bentone® LT, an amine oxide and hydroxyethyl cellulose modified hectorite clay gellant trademark named BENAQUA® as well as highly purified montmorillonite clays sold under the trademark name BEN-A-GEL™ and BEN-A-GEL™ EW.

These hydrophilic gelling agents are recommended by their manufacturer for use in a pH range of 3-11, and gellants such as Bentone® LT have been used for many years to gel the aqueous, alkaline portion of "with base" relaxers which usually have pH values of about 12-13. Bentone® LT was found ineffective to adequately stabilize no-base relaxer formulations.

Lipophilic hectorite clay gellants used for dispersing oils are all organically modified, and several are designated by the trademark names cited hereinbelow. The organically modified lipophilic gelling agents are modified first with a quaternary nitrogen-containing compound and then optionally, by other organic materials. Specific lipophilic gelling agents are comprised of stearalkonium hectorite or quaternium-18 [dimethyl-di-(hydrogenated tallow)-ammonium chloride]hectorite, and are sold as powders under the trademark names Bentone® 27 and Bentone® 38, respectively. When dispersed in organic liquids, these gelling agents are said by the manufacturer to form stable oleaginous gels and water-in-oil emulsions over a pH range of 4-10. The manufacturer also states that prolonged contact at higher or lower pH values can cause decomposition of the gelling agent with a reduction of gel strength.

The preferred lipophilic hectorite clay gellants are those comprised of hectorite clays modified with (1) a quaternary nitrogen-containing compound such as stearalkonium chloride or quaternium-18 which contains at least one long chain ($C_8$-$C_{20}$) substituent on the quaternary nitrogen atom, (2) propylene carbonate, and (3) a non-polar organic liquid. Examples of such non-polar organic liquids include but are not limited to mineral spirits, mineral oil, glycerides, such as castor oil, a mixture of lanolin oil and isopropyl palmitate, and the like. [Stearalkonium chloride and quaternium-18 are defined in the *CTFA Cosmetic Ingredient Dictionary*, 2nd ed., published by The Cosmetic Toiletry and Fragrance Association, Inc. (*CTFA Dictionary*)]

Specific, useful lipophilic gellants that are commercially available as mastergels include: Bentone® Gel MIO, comprised of mineral oil, propylene carbonate and quaterium-18 hectorite; Bentone® Gel CAO, comprised of propylene carbonate, castor oil and stearalkonium hectorite; Bentone® Gels SS71 and S130, comprised of mineral spirits (ligroin or petroleum spirits having a boiling range of about 318 degrees-400 degrees F.), propylene carbonate and quaternium-18 hectorite; and Bentone® Gel Lantrol, comprised of propylene carbonate, a mixture of lanolin oil (dewaxed lanolin) and isopropyl palmitate, and stearalkonium hectorite. The above hectorite gellants can be used individually or mixed together in a composition.

About 3 to about 50, and more preferably about 15 to about 35 weight percent, of the alkaline composition of a contemplated no-base hair relaxer composition is comprised of oleaginous materials including mineral oils, petrolatum and mineral jellies. This range is exclusive of the oleaginous materials contained in the modified hectorite clay gellants that may also be present.

Mineral oils useful herein have Saybolt viscosities at 100° F. of about 50 S.U.S. to about 350 S.U.S. and specific gravities at 60° F. of about 0.828 to about 0.895 (0.828/0.895). The materials having Saybolt viscosities of about 50/60 S.U.S. at 100° F. and specific gravities of about 0.828/0.838 at 60° F. are preferred.

Useful petrolatum is also available in several grades based upon both viscosity, melting point and color. The viscosities of these products are about 50 to about 90 (50/90) S.U.S. at 210° F. (about 100° C.). Preferably, a colorless or "white" product having a Saybolt viscosity of about 55/75 S.U.S. at 210° F. and melting points of about 135° F./140° F. and about 127°/137° F. are used.

In addition, mineral jellies compounded of white mineral oil, petrolatum and wax can also be used as the oleaginous material in the compositions of this invention. Such materials typically have Saybolt viscosities at 210° F. of about 35/46 S.U.S., preferably about 37/40 S.U.S., U.S.P. melting points of about 97°/120° F., and pour points of about 75°/130° F., preferably of about 110°/120° F.

Although the oleaginous materials are typically present at about 3 to about 50 weight percent, the percentage actually used in a product depends upon the desired product consistency as is well-known in the formulation of cosmetic creams. Thus, when a very stiff relaxer is desired, petrolatum is preferred over the less viscous mineral oil and mineral jellies. Whereas mineral jellies are themselves mixtures, mixtures such as petrolatum-mineral oil combinations are also useful for varying the viscosity or stiffness of the cream composition. When a thinner or softer cream is desired, the less viscous oleaginous materials are preferred. Additionally, because a hectorite clay gellant and oleaginous material can both be used to adjust viscosity or stiffness, one can be "played" against the other as is known in the art to obtain a desired cream viscosity.

Various emulsifying agents and mixtures thereof are also typically present in a contemplated hair straightening formulation. These emulsifiers include non-ionic, anionic and amphoteric surfactants, and are present at about 3 to about 15 percent by weight of the total composition.

The use of water-in-oil emulsions and emulsifiers for that purpose is preferred for ease in removal from the hair after the relaxation process is completed. A contemplated relaxer typically has a viscosity of about 100,000 (like sour cream at room temperature) to about 900,000 centipoise (cps) at 25° C., and more preferably about 100,000 to about 250,000 cps (peanut butter at room temperature).

Anionic emulsifiers are illustrated by polyoxyethylene oleyl ether phosphates having about 3 to about 20 oxyethylene groups, sodium lauryl sulfate, and the stearic acid anion and the like. Polyoxyethylene (3) oleyl ether phosphate is particularly preferred. In compounding a phase-stable cream, an anionic emulsifier in substantially non-aqueous form is included in the oil phase at about 0.01 to about 1.0 weight percent, preferably at about 0.1 to about 0.5 weight percent of the total composition.

Suitable non-ionic, $C_2$-$C_8$ polyhydroxy compounds can be used as part of the emulsifying system. Exemplary polyhydroxy compounds include propylene glycol, glycerin, butylene glycol, hexylene glycol, sorbitol and the like can be used. Particularly preferred is propylene glycol. The polyhydroxy compounds can be present at about 0.1 to about 10 weight percent, preferably at about 3 to about 8 weight percent.

Sorbitol is generally preferred as a component of the activator solution for a no-lye hair relaxer.

Other nonionic emulsifying agents useful as the primary emulsifier, are preferably emulsifying waxes that meet the standards of the National Formulary (N.F.) or British Pharmacopeia (B.P.) and can either be the non-self-emulsifying or the self-emulsifying type. The term "emulsifying wax" denotes a solid nonionic emulsifier known in the art that are prepared as a mixture of fatty alcohols having from about 12 to about 24 carbon atoms, preferably predominantly lipophilic fatty alcohols having from about 14 to about 20 carbon atoms.

Self-emulsifying waxes are typically prepared with an auxiliary hydrophilic emulsifier present. The hydrophilic nonionic emulsifiers present in the primary nonionic emulsifier as part of the emulsifying wax are usually polyoxyethylene derivatives of fatty acid esters of sorbitol and sorbitol anhydride. Preferred are polysorbates that generally comprise mixtures of oleate or stearate esters condensed with ethylene oxide.

A preferred N.F. grade emulsifying wax is prepared from cetostearyl alcohol containing a polyoxyethylene derivative of a fatty acid ester of sorbitan. This material is known as Emulsifying Wax N.F. and is a creamy white, wax-like solid that is freely soluble in ether, chloroform, alcohol and most hydrocarbon solvents, but is insoluble in water. It melts at a temperature between 48 degrees and 52 degrees C., has a hydroxyl value of about 178 to about 192, an iodine value not more than 3.5, a saponification value not more than 14, and a pH (in a dispersion of 3 parts in 100 parts of water) of about 5.5 to 7.0. Emulsifying Wax N.F. is commercially available from a number of suppliers. Exemplary and preferred materials are sold under the name POLAWAX by Croda, Inc., New York, N.Y.; and LIPOWAX® P by Lipo Chemicals, Inc., Paterson, N.J.

Other useful emulsifying waxes are commercially available and comprise balanced blends of lipophilic fatty alcohols (some distilled or double distilled) derived from fatty acids containing about 12 to about 24 carbon atoms and ethylene adducts thereof. Particularly preferred are emulsifying waxes containing about 14 to about 20 carbon atoms, more preferably about 16 to about 18 carbon atoms. Alternatively, the primary nonionic emulsifier can be a balanced blend of the individual lipophilic fatty alcohols, having about 14 to about 20 carbon atoms, more preferably about 16 to about 18 carbon atoms. Particularly useful fatty alcohols include cetyl alcohol, pentadecanol, octadecanol oleyl alcohol, tallow fatty alcohols and the like saturated and monounsaturated monovalent linear alcohols obtained from vegetable sources, animal oils and fats.

Particularly preferred are tallow fatty alcohols manufactured and sold under the trademark HYDRENOL® D. or DD by Henkel KGaA, Germany. According to the manufacturer, these materials contain a mixture of mostly $C_{16}$-$C_{18}$ fatty alcohols. Another preferred nonionic emulsifier is a fatty alcohol mixture containing cetyl and stearyl alcohols sold under the trademark TA1618F by The Procter & Gamble Company Industrial Chemicals Divisions, Cincinnati, Ohio.

In the practice of this invention, the nonionic emulsifying agent is generally present at about 3 to about 15 weight percent, preferably at about 5 to about 12, more preferably at about 6 to about 10.

In addition to the before-described non-ionic emulsifiers that can be exemplified by $C_{12}$-$C_{18}$ fatty alcohols, other non-ionic emulsifiers are also contemplated such as lanolin and its polyoxyethylene derivatives such as polyoxyethylene (75) lanolin, polyethylene oxide-polypropylene oxide condensates, polyoxyethylene ethers of fatty alcohols such as polyoxyethylene (20) oleyl ether and the like.

Amphoteric surfactants such as 2-heptadecyl-1-carboxymethyl-1-(2-hydroxyethyl)-2-imidazolinium chloride sold under the trademark designation Miranol® DM by the Miranol Chemical Company, Inc. The preferred amphoteric emulsifier, 2-heptadecyl-1-carboxymethyl-1-(2-hydroxyethyl)-2-imidazolinium chloride or stearoamphoglycinate, its *CTFA Dictionary* name, can be present from about 0.25 to about 10 weight percent and preferably at about 0.25 to about 5 weight percent of the total composition. This amphoteric emulsifier is particularly useful for hair relaxing compositions that also condition the hair, leaving it soft and manageable as well as straightening it. Water-soluble, quaternary, cationic polymers that modify the hair surface characteristics and thereby improve the hair feel and ease of combing can be used as such hair conditioners or conditioning agents.

Suitable additional amphoteric surfactants include alkylamphocarboxyproprionates, and alkylamphoglycinates having mono- or di-carboxyl groups derived from fatty acids having about 10 to about 22 carbon atoms in the fatty alkyl chain.

Additional amphoteric or zwitterionic emulsifiers include the class of surface active agents having an aminopropionate structure, such as N-fatty alkyl beta propionic acid and alkali metal salts thereof. Commercial materials having lauryl, myristyl, coca and tallow fatty alkyl groups are sold commercially under the tradename DERIPHAT® by General Mills Chemicals, Inc., Cosmedia Group, Minneapolis, Minn.

U.S. Pat. No. 4,175,572 discloses hair conditioning compositions that can be used in conjunction with highly alkaline hair waving or straightening compositions based on sodium hydroxide or a similar alkaline material. The conditioner described therein can be combined with the waving or relaxing formulation prior to use, or can be applied separately to the hair either before or after application of the relaxer composition. The compositions therein disclosed contain a conditioning agent comprised of a cationic quaternary nitrogen-containing polymer having diallyldimethylammonium chloride or bromide repeating units.

No-base relaxer compositions can be prepared that comprise the above described amphoteric emulsifier and conditioning cationic polymer as well as an organically modified, lipophilic hectorite gellant to provide a unitary product that relaxes the hair and conditions it while maintaining compositional stability and therefore shelf life. These stable conditioning no-base relaxers have compositions similar to those described hereinabove with the exception that the polymers having the above-described repeating unit are also present at about 0.05 to about 8 weight percent and preferably about 0.5 to about 2 weight percent along with the above-described amphoteric emulsifier.

Homopolymers having the above repeating units are preferred conditioning agents. These polymers can be prepared by polymerizing diallyldimethylammonium chloride or bromide, or other suitable diallyldimethylammonium salts, using a free radical generating polymerization catalyst, such as a peroxide or hydroperoxide, then employing a suitable an ion exchange resin, if desired, according to the methods described in U.S. Pat. No. 3,288,770 and No. 3,412,091. The resulting polymers are polydiallyldimethylammonium salts, such as polydiallyldimethylammonium chloride.

Homopolymers and copolymers of polydiallyldimethylammonium chloride are available in aqueous compositions sold under the trademark MERQUAT® by E. M. Merck & Co. The homopolymer that is named polyquaternium-6 in the *CTFA Dictionary* and is trademarked MERQUAT®-100 is particularly preferred. However, a copolymer reaction product of diallyldimethylammonium chloride with acrylamide monomers, named polyquaternium-7 in the *CTFA Dictionary* and sold under the trademark MERQUAT®-550 can also be used. It is understood that a number of other cationic polymeric conditioning agents are commercially available and known that can also be used, the disclosure of the preferred cationic polymer is not intended to limit the scope of this invention.

A hair relaxer composition can also include cosmetic adjuvants, such as auxiliary emollients, auxiliary thickening agents, perfumes, preservatives, and product colorants present in the cosmetic cream base composition, in the activator, or in both. These cosmetic adjuvants are well known in the art.

The present invention also contemplates an improved method for straightening hair, and particularly grey or white hair. In a contemplated method, an aqueous hair relaxer composition containing active straightening ingredients and excipients as discussed above is applied to the hair.

The relaxer-containing hair thereby formed is physically smoothed. It is believed that the smoothing of the relaxer-containing hair stresses the individual hair fibers and causes a realignment of the sulfur atom-containing groups within those fibers, presumably after breaking the disulfide bonds, so that the sulfur-containing groups within the hair have a new, straightened configuration after the sulfur-containing bonds are remade as lanthionine groups rather than the original cystines.

The relaxer is maintained in contact with the hair and the hair is maintained smoothed (under longitudinal stress) for a time period sufficient for hair straightening to occur. That maintenance time period typically varies with the degree of initial tightness of the curled hair to be straightened, and the degree of straightening desired, as well as the product used for straightening. Usual time periods are about 5 minutes for slightly curly hair to about 30 minutes for tightly curled hair to achieve optimal straightening. A skilled cosmetologist having experience with various hair straightening products and the degree of curl of subjects' hair can readily determine the appropriate duration of maintenance time to use. Use of a contemplated aqueous relaxer composition has not been found to alter the time required to effect straightening is the compositions examined to date.

Upon completion of the desired maintenance time, the relaxed hair rinsed, shampooed, and dried. Comparisons of half-head treatments using the invention versus otherwise identical commercial relaxers have indicated no difference in straightening effect. However, when used on grey or white human hair, a contemplated aqueous relaxer composition provided maintenance of the original grey or white color as compared to usual products that cause such hair to become discolored.

ILLUSTRATIVE EXAMPLES

A. Compositions

1. No-Lye Relaxer

To a jar of commercial aqueous No-Lye relaxer is added sodium formaldehyde sulfoxylate to provide a composition with the following final concentration of components:
1. Calcium hydroxide percent by weight=4.73%
2. Guanidine hydroxide percent by weight=5.28% (Guanidine monohydrate)
3. Sodium formaldehyde sulfoxylate=4.22%
   2. No-Lye Crème Relaxer A jar commercial of No-Lye Crème Relaxer contains a total of 213 gm of an aqueous relaxer composition, of which 6.00% is Ca(OH)$_2$=12.8 gm. To that Crème Relaxer is added a mixture 57.0 gm of which 25.0% is guanidine hydroxide=14.3 gm and 11.4 gm is sodium formaldehyde sulfoxylate to provide a contemplated relaxer composition.

3. Lye Relaxer

To a jar of commercial aqueous Lye relaxer is added sodium formaldehyde sulfoxylate to provide a composition with the following final concentration of components:
1. Sodium hydroxide percent by weight=1.63%
2. Guanidine hydroxide percent by weight=0.10% (Guanidine monohydrate)
3. Sodium formaldehyde sulfoxylate percent by weight=4.20%
   4. Lye Crème Relaxer A jar of commercial aqueous Lye Crème Relaxer contains a total of 226.8 gm, of which 2.10% is NaOH=4.763 gm. To that Crème Relaxer is added a mixture 57 gm of a 0.5% is guanidine hydroxide=0.285 gm that also contains sodium formaldehyde sulfoxylate added @20.0%, or =11.4 gm to provide a completed Lye Crème Relaxer.

5. No-Lye Crème Relaxer

A jar of commercial No-Lye Crème Relaxer contains a total of 226.8 gm of aqueous composition, of which 1.75% is KOH=3.97 gm. To that Crème Relaxer is added a mixture 57.0 gm of a 0.5% is guanidine hydroxide=0.285 gm that also contains sodium formaldehyde sulfoxylate added @20%, or =11.4 gm to provide a completed No-Lye Crème Relaxer.

6. No-Lye Relaxer

A jar of No-Lye Relaxer is prepared that contains the following along with water and thickening agents, oleaginous materials, gellants, emulsifiers and odorants as excipients:
1. Potassium hydroxide percent by weight=1.398%
2. Guanidine hydroxide percent by weight=0.10% (guanidine monohydrate)
3. Sodium formaldehyde sulfoxylate percent by weight=4.20%
   7. No-Lye Relaxer A jar of No-Lye Relaxer is prepared that contains the following along with water and thickening agents, oleaginous materials, gellants, emulsifiers and odorants as excipients:
1. Calcium hydroxide by weight=4.73%
2. Guanidine hydroxide by weight=5.28% (guanidine monohydrate)
3. Disodium salts of 2-hydroxy-2-sulfinatoacetic acid and 2-hydroxy-2-sulfoacetic acid percent by weight=5.01%
   8. No-Lye Relaxer Crème Relaxer A jar commercial of No-Lye Crème Relaxer contains a total of 213 gm of aqueous relaxer composition, of which 6% is Ca(OH)$_2$=12.78 gm. To that Crème Relaxer is added a mixture 57 gm of which 25% is guanidine hydroxide=14.25 gm and 3.42 gm is a mixture of disodium salts of 2-hydroxy-2-sulfinatoacetic acid and 2-hydroxy-2-sulfoacetic acid at 6% by weight to provide a contemplated relaxer composition.

9. Lye Relaxer

A jar of aqueous No-Lye Relaxer is prepared that contains the following along with water and thickening agents, oleaginous materials, gellants, emulsifiers and odorants as excipients:
1. Potassium hydroxide percent by weight=1.398%
2. Guanidine hydroxide percent by weight=0.10% (guanidine monohydrate)
3. Disodium salts of 2-hydroxy-2-sulfinatoacetic acid and 2-hydroxy-2-sulfoacetic acid=5.01%
   10. Lye Crème Relaxer A jar of commercial aqueous Lye Crème Relaxer contains a total of 226.8 gm, of which 2.1% is NaOH=4.763 gm. To that Crème Relaxer is added a mixture 57 gm of a 0.5% is guanidine hydroxide=0.285 gm that also contains a mixture of disodium salts of 2-hydroxy-2-sulfinatoacetic acid and 2-hydroxy-2-sulfoacetic acid at 6% is =3.42 gm to provide a completed Lye Crème Relaxer.

11. No-Lye Relaxer

A jar of commercial aqueous No-Lye relaxer has the following:
1. Potassium hydroxide percent by weight=1.24%
2. Guanidine hydroxide percent by weight=0.37% (Guanidine monohydrate)
3. Disodium salts of 2-hydroxy-2-sulfinatoacetic acid and 2-hydroxy-2-sulfoacetic acid=5.01%

12. No-Lye Crème Relaxer

A jar of commercial aqueous No-Lye Crème Relaxer contains a total of 226.8 gm, of which 1.75% is KOH=3.969 gm. To that Crème Relaxer is added a mixture 57 gm of a 1.5% is guanidine hydroxide=0.855 gm that also contains a mixture of disodium salts of 2-hydroxy-2-sulfinatoacetic acid and 2-hydroxy-2-sulfoacetic acid at 6% is =3.42 gm to provide a completed No-Lye Crème Relaxer.

EXAMPLE 1

No-Lye Relaxer with Hair Brightener Hair Type History

| | |
|---|---|
| Number of heads: | Two (2) |
| Hair Texture range: | One (1) Medium One (1) Coarse |
| Chemically Treated: | Two (2) |
| Color Treated: | None |
| Scalp Condition: | Two (2) Healthy |
| Hair Length: | Two (2) Medium |

Objective:

To assess three applications of this No-Lye relaxer with hair brightener on white and grey hair types of living humans. This composition was applied on half-head bases.

Project Description:

(Optimum Care® No-Lye Relaxer with Hair Brightener Additive-Vs-Optimum Care® No-Lye Relaxer without any Additives)

Composition Application:

Optimum Care® No-Lye relaxer (Soft Sheen-Carson Products, New York, N.Y.) was purchased from a beauty product supply store. Using the same bottles found in the relaxer kit, the guanidine carbonate solution (composition number 2) was replaced with the same weight guanidine carbonate as that found in the kit plus brightener, sodium formaldehyde sulfoxylate in an amount sufficient to provide 5 percent by weight to the solution for application to the head. FD& C Red #40 was added to the guanidine carbonate plus brightener solution to make the two products indistinguishable to the cosmetologist. The two types of relaxer were (one that contained the brightener and control) were applied to heads from kit jars.

Compositions were applied to the subjects' hair without identification by a licensed cosmetologist. After application of the compositions, the hair was physically smoothed to apply tension and presumably realign the sulfur atoms within the fibers. The hair was maintained smoothed for a time period sufficient for hair straightening to occur based on the cosmetologist's experience.

The results discussed below were obtained from three separate administrations of relaxer to the same two individuals on day zero, about three months later and one year after the first treatment. The only difference noted among the three treatments was that there was no discernible difference in viscosity or dripping between the test composition and the control during the first administration, but a slight thinning and slight dripping were noted during the second and third administrations for the composition containing the brightener. This thinning was addressed by the addition of 0.10% xanthan gum to composition number 2.

The relaxer treatments were carried out pursuant to the instructions for the commercial product. Pretreatment using Optimum Care® Salon Collection Protective Pre-treatment was applied to the ends of the hair prior to application of the relaxers. Relaxers were applied to each half head following the package instructions and permitted to process for 15-16 minutes on both subjects. After processing was completed, both relaxer products were rinsed from the hair. Optimum Care® Salon Collection Neutralizing Shampoo was applied globally for two (2) applications. After neutralization, Optimum Care® Salon Collection Reconstructor Treatment was applied to the hair and permitted to process for ten (10) minutes, followed by a complete rinse. The Optimum Care® Salon Collection Leave-In Strengthener was applied through out the hair and left in for 5 minutes and towel blotted dry before placing the subject under the dryer. After drying, the Optimum Care® Salon Collection Whipped Oil Moisturizer was applied while blow drying and curling. Hair discoloration was monitored during and after the relaxing process.

The products used were easily identified by observation. The white hair was significantly yellow to tan in color where product without brightener in composition number 2 was used, whereas the hair treated with brightener in composition number 2 was white.

Product Aspects:

Consistency of the control sample without the brightener was observed as being slightly thicker less runny. During mixing and after completion of adding the composition number 2 without the xanthan gum the consistency was noted as being thinner, a little runny. This runniness created a little product fall off during the application and made pull through of the hair a bit easier, there was no scalp sensation with either sample.

Wet Hair Observations:

Smoothness of wet hair, suppleness of wet hair, wet hair detangling, wet hair combing, coating amount and type were all noted as being equal in comparison. The areas treated with the commercial relaxer without brightener were observed to have yellow to yellowish tan discoloration in the new growth areas. These observations have been consistently observed each time this test has been conducted. Shimmer Lights™ rinse-out conditioner was applied to these areas to remove the discoloration on the side without the brightener. The sides of the head treated with the Relaxer with brightener were noted as being free of any discoloration in the new growth areas.

Dry Hair Observations:

Substantially no differences were noted between the hair processed by either treatment for the first two administrations. After the third administration, blow drying was slightly easier on the sides treated with the relaxer with brightener. These areas were also noted as being just a little straighter in relaxation, a bit smoother feeling, a little less resistant to dry combing, having a bit more body and slightly more individualized hairs. These differences were very slight and would not be observed by the average consumer. Mass effect of dry hair, visual smoothness, suppleness, volume, lack of breakage, coating amount, coating type, ease of shaping with iron, lack of sticking to iron, sizzle, smoke and final scalp conditioner were all noted as being comparable to equal in comparison. No noticeable differences in these areas.

Conclusion:

Overall preference was for the relaxer modified with brightener. This system did not require any additional steps (application of Shimmer Lights™ conditioner) during the relaxing process. Results indicate that yellow to yellowish green discoloration occurs in the new growth areas during the relaxing process, which requires the use of products designed to brighten white/grey hair (Shimmer Lights™ by Clairol or Yellow Out® by Bantu®).

Although most subjects are accustomed to having to use additional products to remove this discoloration, the relaxer with brightener eliminates this process. However it has been consistently observed that the viscosity of the relaxer plus activator with brightener becomes a bit thin and runny after mixing. This impacts product fall off during application but does not indicate any other issues during the relaxing process.

EXAMPLE 2

Relaxer Test with Hair Brightener

Two half-head relaxer studies were done using Naked Relaxer System by Essations® of Clintex Laboratories of Chicago, Ill., a sodium hydroxide relaxer. A 220 gm aliquot from a 4 pound container to which a 57 gm mixture containing 25% as guanidine hydroxide=14.25 gm and 11.4 gm of sodium formaldehyde sulfoxylate was added to provide a contemplated relaxer composition.

This composition was mixed for approximately 30 seconds before applying to the hair on one-half the head of a 64 year old male whose hair is about 50% gray. The other head side was relaxed using 220 gm of the Naked Relaxer System by Essations® relaxer without any additive.

The relaxers were applied evenly, the hair fibers stressed by smoothing, and the relaxers were maintained in contact with the smoothed hair for 15 minutes. There was no notable difference in viscosity of the two samples. The relaxer was then rinsed out and the hair evaluated after towel drying.

The side using the added mixture of sulfinomethanolate hydrate and guanidine carbonate was white with no sign of color change. The side without the additive was yellow and slightly blond in color. There was no noticeable difference in smoothness or hair texture on the side to which the additive was added after the Naked Relaxer System by Essations® Conditioner was applied evenly to the whole head.

Eight weeks later another half-head study was done using TCB® relaxer Of Unilever, London, GB, a sodium hydroxide relaxer. A 220 gm aliquot from a 1 pound container to which a 57 gm mixture containing 25% as guanidine hydroxide=14.25 gm and 11.4 gm of sodium formaldehyde sulfoxylate was added to provide a contemplated relaxer composition. This combination was mixed for approximately 35 seconds before applying to the hair on one side of the above subject's head, the hair on which had approximately 1 inch of new growth.

Following the commercial product package instructions, the other head side was relaxed using the TCB® relaxer with no additive. After the completion of the relaxation process, the hair on the head side without the additive was yellowish green in color. The hair of the head side with the additive was white with no color changes to the hair. There was no noticeable change in the relaxer consistency or performance. There was no difference in smoothness the cuticle or loss of hair.

All administrations were carried out by a licensed Cosmetologist who uses relaxers as a normal work regimen.

Each of the patents, patent applications and articles cited herein is incorporated by reference. The use of the article "a" or "an" is intended to include one or more.

The foregoing description and the examples are intended as illustrative and are not to be taken as limiting. Still other variations within the spirit and scope of this invention are possible and will readily present themselves to those skilled in the art.

The invention claimed is:

1. In a hair relaxer comprising an aqueous composition of active human hair straightening ingredients and excipients having a pH value of about 12 to about 14, the improvement that comprises a naturally grey or white human hair discoloration-inhibiting amount of an alpha-hydroxy-$C_1$-$C_6$ sulfinate of Formula I dissolved or dispersed in said relaxer in

addition to said active straightening ingredients and excipients, wherein $R^1$ and $R^2$ are the same or different and are hydrogen (hydrido) or hydrocarbyl, or one of $R^1$ and $R^2$ is carboxy or carboxy-substituted hydrocarbyl and the other is hydrido or hydrocarbyl that together ($R^1$+$R^2$) contain a total of five carbon atoms, or $R^1$ and $R^2$ together with the depicted carbon atom form a ring structure that can contain up to six carbon atoms, and M is a proton or a cosmetically acceptable cation such as an ammonium ion, a monovalent metal ion or an equivalent of a divalent metal ion of the Groups Ia, IIa, IIb, IVa or VIIIb of the Periodic Table of the Elements.

2. The improved hair relaxer according to claim 1, wherein said alpha-hydroxy-$C_1$-$C_6$ sulfinate has the structure of Formula III

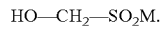

3. The improved hair relaxer according to claim 1, wherein said alpha-hydroxy-$C_1$-$C_6$ sulfinate is an alpha-hydroxy-$C_1$-$C_6$-carboxy sulfinate of Formula II

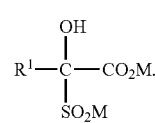

4. The improved hair relaxer according to claim 3, wherein said alpha-hydroxy-$C_1$-$C_6$-carboxy sulfinate is a compound of Formula IV

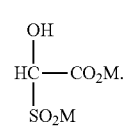

5. The hair relaxer according to claim 1, wherein said alpha-hydroxy-$C_1$-$C_6$ sulfinate is present in an amount that provides an equivalent of about 4 to about 6 weight percent of sodium sulfinomethanolate based upon the total weight of relaxer composition applied to the hair.

6. An aqueous hair relaxer composition having a pH value of about 12 to about 14 comprising i) an aqueous composition of active human hair straightening ingredient, ii) a cosmetically useful amount of excipient, and iii) a naturally grey or white human hair discoloration-inhibiting amount an alpha-hydroxy-$C_1$-$C_6$ sulfinate of Formula I in addition to said active straightening

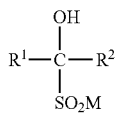   I ingredients and excipients, wherein
   $R^1$ and $R^2$ are the same or different and are hydrogen (hydrido) or hydrocarbyl, or
   one of $R^1$ and $R^2$ is carboxy or carboxy-substituted hydrocarbyl and the other is hydrido or hydrocarbyl that together ($R^1$+$R^2$) contain a total of five carbon atoms, or
   $R^1$ and $R^2$ together with the depicted carbon atom form a ring structure that can contain up to six carbon atoms, and
   M is a proton or a cosmetically acceptable cation such as an ammonium ion, a monovalent metal ion or an equivalent of a divalent metal ion of the Groups Ia, IIa, IIb, IVa or VIIIb of the Periodic Table of the Elements.

7. The hair relaxer according to claim 6, wherein said alpha-hydroxy-$C_1$-$C_6$ sulfinate being dissolved or dispersed in said relaxer in an amount that provides an equivalent of about 4 to about 6 weight percent of sodium sulfinomethanolate based upon the total weight of relaxer composition applied to the hair.

8. The hair relaxer according to claim 6, wherein M is sodium or potassium.

9. The hair relaxer according to claim 6 that is formulated as a no-lye relaxer in which said active human hair straightening ingredient is a mixture of an alkaline earth hydroxide and an amidino group-containing organic base.

10. The hair relaxer according to claim 6 that is formulated as a no-base, no-lye relaxer.

11. The hair relaxer according to claim 6, in which said active human hair straightening ingredient is an alkali metal hydroxide.

12. The hair relaxer according to claim 11, wherein said alkali metal hydroxide is sodium hydroxide.

13. The hair relaxer according to claim 6, wherein said alpha-hydroxy-$C_1$-$C_6$ sulfinate is disodium 2-hydroxy-2-sulfinatoacetate.

14. The hair relaxer according to claim 6, wherein said alpha-hydroxy-$C_1$-$C_6$ sulfinate is sodium sulfinomethanolate.

15. In a method of straightening naturally grey or white human hair with an aqueous hair relaxer composition containing active straightening ingredients and excipients in which said relaxer composition is applied to the hair, the hair is physically smoothed and maintained smoothed for a time period sufficient for hair straightening to occur, rinsed, shampooed, and dried, the improvement which comprises using the aqueous human hair relaxing composition according to claim 1.

16. The method according to claim 15, wherein said alpha-hydroxy-$C_1$-$C_6$ sulfinate has the structure of Formula III

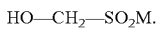   III

17. The method according to claim 15, wherein said alpha-hydroxy-$C_1$-$C_6$ sulfinate is an alpha-hydroxy-$C_1$-$C_6$-carboxy sulfinate of Formula II

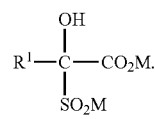   II

18. The method according to claim 17, wherein said alpha-hydroxy-$C_1$-$C_6$ sulfinate is a compound of Formula IV

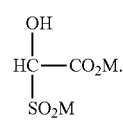   IV

19. The method according to claim 15, wherein said alpha-hydroxy-$C_1$-$C_6$ sulfinate is present in an amount that provides an equivalent of about 4 to about 6 weight percent of sodium sulfinomethanolate based upon the total weight of relaxer composition applied to the hair.

* * * * *